(12) United States Patent
Borsini et al.

(10) Patent No.: US 10,098,876 B2
(45) Date of Patent: *Oct. 16, 2018

(54) TREATING SEXUAL DESIRE DISORDERS WITH FLIBANSERIN

(71) Applicant: Sprout Pharmaceuticals, Inc., Bridgewater, NJ (US)

(72) Inventors: Franco Borsini, Bad Waldsee (DE); Kenneth Robert Evans, Toronto (CA)

(*) Notice: Subject to any disclaimer, the term of this patent is extended or adjusted under 35 U.S.C. 154(b) by 0 days.

This patent is subject to a terminal disclaimer.

(21) Appl. No.: 15/694,317

(22) Filed: Sep. 1, 2017

(65) Prior Publication Data

US 2018/0055839 A1   Mar. 1, 2018

Related U.S. Application Data

(63) Continuation of application No. 15/270,167, filed on Sep. 20, 2016, now Pat. No. 9,782,403, which is a continuation of application No. 14/640,055, filed on Mar. 6, 2015, now Pat. No. 9,468,639, which is a continuation of application No. 14/269,373, filed on May 5, 2014, which is a continuation of application No. 13/920,354, filed on Jun. 18, 2013, which is a continuation of application No. 13/551,036, filed on Jul. 17, 2012, which is a continuation of application No. 11/524,268, filed on Sep. 21, 2006, now Pat. No. 8,227,471, which is a continuation of application No. 10/272,603, filed on Oct. 16, 2002, now Pat. No. 7,151,103.

(60) Provisional application No. 60/348,911, filed on Oct. 23, 2001.

(30) Foreign Application Priority Data

Oct. 20, 2001   (EP) ........................... 01125020

(51) Int. Cl.
A61K 31/496   (2006.01)

(52) U.S. Cl.
CPC .................. *A61K 31/496* (2013.01)

(58) Field of Classification Search
CPC .................................................. A61K 31/496
See application file for complete search history.

(56) References Cited

U.S. PATENT DOCUMENTS

| | | | | |
|---|---|---|---|---|
| 6,083,947 A * | 7/2000 | Granger | ............. | A61K 31/00 514/249 |
| 7,151,103 B2 * | 12/2006 | Borsini | ............. | A61K 31/496 514/254.06 |
| 7,183,410 B2 * | 2/2007 | Bombarda | ......... | C07D 233/26 544/295 |
| 8,227,471 B2 * | 7/2012 | Borsini | ............. | A61K 31/496 514/254.06 |
| 9,468,639 B2 * | 10/2016 | Borsini | ............. | A61K 31/496 |
| 9,782,403 B2 * | 10/2017 | Borsini | ............. | A61K 31/496 |

* cited by examiner

*Primary Examiner* — Trevor Love

(57) ABSTRACT

The invention relates to the use of flibanserin, or a pharmaceutically acceptable acid addition salt thereof, for the treatment of disorders of sexual desire.

20 Claims, No Drawings

TREATING SEXUAL DESIRE DISORDERS WITH FLIBANSERIN

RELATED APPLICATIONS

This application is a continuation of U.S. patent application Ser. No. 15/270,167 for TREATING SEXUAL DESIRE DISORDERS WITH FLIBANSERIN, filed Sep. 20, 2016, which is a continuation of U.S. patent application Ser. No. 14/640,055 for TREATING SEXUAL DESIRE DISORDERS WITH FLIBANSERIN, filed Mar. 6, 2015, now U.S. Pat. No. 9,468,639, which is a continuation of U.S. patent application Ser. No. 14/269,373 for TREATING SEXUAL DESIRE DISORDERS WITH FLIBANSERIN, filed May 5, 2014, which is a continuation of U.S. patent application Ser. No. 13/920,354 for TREATING SEXUAL DESIRE DISORDERS WITH FLIBANSERIN, filed Jun. 18, 2013, which is a continuation of U.S. patent application Ser. No. 13/551,036 for TREATING SEXUAL DESIRE DISORDERS WITH FLIBANSERIN, filed Jul. 17, 2012, which is a continuation of U.S. patent application Ser. No. 11/524,268 for TREATING SEXUAL DESIRE DISORDERS WITH FLIBANSERIN, filed Sep. 21, 2006, now U.S. Pat. No. 8,227,471, which is a continuation of U.S. patent application Ser. No. 10/272,603, for METHOD OF TREATING FEMALE HYPOACTIVE SEXUAL DESIRE DISORDER WITH FLIBANSERIN, filed Oct. 16, 2002, now U.S. Pat. No. 7,151,103, which claims the benefit (i) of U.S. Provisional Patent Application Ser. No. 60/348,911 for SEXUAL DESIRE ENHANCING MEDICAMENTS, filed Oct. 23, 2001, and (ii) European Patent Application No. EP 01 1250 20.6 for USE OF FLIBANSERIN IN THE TREATMENT OF SEXUAL DISORDERS, filed Oct. 20, 2001. This nonprovisional application claims the benefit of and incorporates entirely by reference these U.S. nonprovisional patent applications, U.S. provisional patent application, and European patent application.

FIELD OF THE INVENTION

The invention relates to the use of flibanserin for the preparation of a medicament for the treatment of disorders of sexual desire.

BACKGROUND OF THE INVENTION

The compound 1-[2-(4-(3-trifluoromethyl-phenyl)piperazin-1-yl)ethyl]-2,3-dihydro-1H-benzimidazol-2-one (flibanserin) is disclosed in form of its hydrochloride in European Patent Application EP-A-526434 and has the following chemical structure:

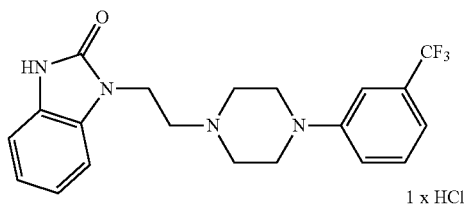 [SMILES: O=c1[nH]c2ccccc2n1CCN1CCN(c2cccc(C(F)(F)F)c2)CC1]

1 x HCl

Flibanserin shows affinity for the 5-HT1A and 5-HT2-receptor. It is therefore a promising therapeutic agent for the treatment of a variety of diseases, for instance depression, schizophrenia, and anxiety.

DETAILED DESCRIPTION OF THE INVENTION

In studies of male and female patients suffering from sexual dysfunction it has been found that flibanserin optionally in form of the pharmacologically acceptable acid addition salts thereof displays sexual desire enhancing properties. Accordingly, the instant invention relates to the use of flibanserin, optionally in form of the pharmacologically acceptable acid addition sails thereof for the preparation of a medicament for the treatment of disorders of sexual desire.

In a preferred embodiment the invention relates to the use of flibanserin, optionally in form of the pharmacologically acceptable acid addition salts thereof for the preparation of a medicament for the treatment of disorders selected from the group consisting of Hypoactive Sexual Desire Disorder, loss of sexual desire, lack of sexual desire, decreased sexual desire, inhibited sexual desire, loss of libido, libido disturbance, and frigidity.

Particular preferred according to the invention is the use of flibanserin, optionally in form of the pharmacologically acceptable acid addition salts thereof for the preparation of a medicament for the treatment of disorders selected from the group consisting of Hypoactive Sexual Desire Disorder, loss of sexual desire, lack of sexual desire, decreased sexual desire, inhibited sexual desire.

In a particularly preferred embodiment the invention relates to the use of flibanserin, optionally in form of the pharmacologically acceptable acid addition salts thereof for the preparation of a medicament for the treatment of disorders selected from the group of Hypoactive Sexual Desire Disorder and loss of sexual desire.

The observed effects of flibanserin can be achieved in men and women. However, according to a further aspect of the invention the use of flibanserin optionally in form of the pharmacologically acceptable acid addition salts thereof for the preparation of a medicament tor the treatment of female sexual dysfunction is preferred.

The beneficial effects of flibanserin can be observed regardless of whether the disturbance existed lifelong or was acquired, and independent of etiologic origin (organic—both, physically and drug induced-, psychogen, a combination of organic—both, physically and drug induced-, and psychogen, or unknown).

Flibanserin can optionally used in form of its pharmaceutically acceptable acid addition salts. Suitable acid addition salts include for example those of the acids selected from, succinic acid, hydrobromic acid, acetic acid, fumaric acid, maleic acid, methanesulphonic acid, lactic acid, phosphoric acid, hydrochloric acid, sulphuric acid, tartaric acid and citric acid. Mixtures of the abovementioned acid addition salts may also be used. From the aforementioned acid addition salts the hydrochloride and the hydrobromide, particularity the hydrochloride, are preferred.

Flibanserin, optionally used in form of its pharmaceutically acceptable acid addition salts, may be incorporated into the conventional pharmaceutical preparation in solid, liquid or spray form. The composition may, for example, be presented in a form suitable for oral, rectal, parenteral administration or for nasal inhalation: preferred forms includes for example, capsules, tablets, coated tablets, ampoules, suppositories and nasal spray. The active ingredient may be incorporated in excipients or carriers conventionally used in pharmaceutical compositions such as, for example, talc, arabic gum, lactose, gelatine, magnesium stearate, corn starch, acqueous or non acqueous vehicles, polyvynil pyrrolidone, semisynthetic glicerides of fatty acids, benzalconium chloride, sodium phosphate, EDTA, polysorbate 80. The compositions are advantageously formulated in dosage units, each dosage unit being adapted to supply a single dose of the active ingredient. The dosis range applicable per day is between 0.1 to 400, preferably between 1.0 to 300, more preferably between 2 to 200 mg.

Each dosage unit may conveniently contain from 0.01 mg to 100 mg, preferably 0.1 to 50 mg.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g of. a flavouring such as vanilline or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g of. with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

The Examples which follow illustrate the present invention without restricting its scope:

Examples of pharmaceutical formulations

| A) Tablets | per tablet |
|---|---|
| flibanserin hydrochloride | 100 mg |
| lactose | 240 mg |
| corn starch | 340 mg |
| polyvinylpyrrolidone | 45 mg |
| magnesium stearate | 15 mg |
| | 740 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| flibanserin hydrochloride | 80 mg |
| corn starch | 190 mg |
| lactose | 55 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

| C) Coated tablets | per coated tablet |
|---|---|
| flibanserin hydrochloride | 5 mg |
| corn starch | 41.5 mg |
| lactose | 30 mg |
| polyvinylpyrrolidone | 3 mg |
| magnesium stearate | 0.5 mg |
| | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

| D) Capsules | per capsule |
|---|---|
| flibanserin hydrochloride | 150 mg |
| Corn starch | 268.5 mg |
| Magnesium stearate | 1.5 mg |
| | 420 mg |

The substance and corn starch are mixed and moistened with water. The moist mass is screened and dried. The dry granules are screened and mixed with magnesium stearate. The finished mixture is packed into size I hard gelatine capsules.

| E) Ampoule solution | |
|---|---|
| flibanserin hydrochloride | 50 mg |
| sodium chloride | 50 mg |
| water for inj. | 5 ml |

The active substance dissolved in water at its own pH or optionally at pH 5.5 to 6.5 and sodium chloride is added to make it isotonic. The solution is filtered free from pyrogens and the filtrate is transferred under aseptic conditions into ampoules which are then sterilised and sealed by fusion.

| F) Suppositories | |
|---|---|
| flibanserin hydrochloride | 50 mg |
| solid fat | 1650 mg |
| | 1700 mg |

The hard fat is melted. At 40° C. the ground active substance is homogeneously dispersed. It is cooled to 38° C. and poured into slightly chilled suppository moulds.

The invention claimed is:

1. A method of treating lack of sexual desire or loss of sexual desire in a patient, comprising administering a therapeutically effective amount of flibanserin or a pharmaceutically acceptable acid addition salt thereof to said patient to treat lack of sexual desire or loss of sexual desire in said patient.

2. The method according to claim 1, wherein the patient is female.

3. The method according to claim 1, wherein the patient is male.

4. The method according to claim 1, wherein the amount administered is between about 0.1 mg and 400 mg per day of flibanserin or a pharmaceutically acceptable acid addition salt thereof.

5. The method according to claim 1, wherein the amount administered is between about 1 mg and 300 mg per day of flibanserin or a pharmaceutically acceptable acid addition salt thereof.

6. The method according to claim 1, wherein the amount administered is in a dosage unit containing between about 0.01 mg and 100 mg of flibanserin or a pharmaceutically acceptable acid addition salt thereof.

7. The method according to claim 1, wherein the amount administered is in a dosage unit containing between about 0.1 mg and 50 mg of flibanserin or a pharmaceutically acceptable acid addition salt thereof.

8. A method of treating a lack of sexual desire in a patient, comprising administering a therapeutically effective amount of flibanserin or a pharmaceutically acceptable acid addition salt thereof to said patient to treat lack of sexual desire in said patient.

9. The method according to claim 8, wherein the patient is female.

10. The method according to claim 8, wherein the patient is male.

11. The method according to claim 8, wherein the amount administered is between about 2 mg and 200 mg per day of flibanserin or a pharmaceutically acceptable acid addition salt thereof.

12. The method according to claim 8, wherein the amount administered is between about 0.1 mg and 100 mg per day of flibanserin or a pharmaceutically acceptable acid addition salt thereof.

13. The method according to claim 8, wherein the amount administered is in a dosage unit containing about 150 mg per day of flibanserin or a pharmaceutically acceptable acid addition salt thereof.

14. A method of treating loss of sexual desire in a patient, comprising administering a therapeutically effective amount of flibanserin or a pharmaceutically acceptable acid addition salt thereof to said patient to treat loss of sexual desire in said patient.

15. The method according to claim 14, wherein the patient is female.

16. The method according to claim 14, wherein the patient is male.

17. The method according to claim 14, wherein the amount administered is between about 0.1 mg and 400 mg per day of flibanserin or a pharmaceutically acceptable acid addition salt thereof.

18. The method according to claim 14, wherein the amount administered is in a dosage unit containing about 100 mg of flibanserin or a pharmaceutically acceptable acid addition salt thereof.

19. The method according to claim 14, wherein the amount administered is in a dosage unit containing about 80 mg of flibanserin or a pharmaceutically acceptable acid addition salt thereof.

20. The method according to claim 14, wherein the amount administered is in a dosage unit containing about 50 mg of flibanserin or a pharmaceutically acceptable acid addition salt thereof.

* * * * *